United States Patent [19]

Maunders et al.

[11] Patent Number: 5,550,309
[45] Date of Patent: Aug. 27, 1996

[54] PROCESS FOR DEHYDROGENATION OF HYDROCARBON FEEDS

[75] Inventors: Barry M. Maunders; Stephen R. Partington, both of Surrey, United Kingdom

[73] Assignee: BP Chemicals Limited, London, England

[21] Appl. No.: 331,815

[22] Filed: Oct. 31, 1994

Related U.S. Application Data

[63] Continuation of Ser. No. 113,097, Aug. 30, 1993, abandoned.

[30] Foreign Application Priority Data

Sep. 4, 1992 [GB] United Kingdom ............... 9218823

[51] Int. Cl.$^6$ .................. C07C 5/32; C07C 1/20; C07C 45/29
[52] U.S. Cl. .................. 585/654; 568/383; 568/449; 585/640; 585/660
[58] Field of Search .................. 585/629, 630, 585/654, 658, 638, 639, 640, 660, 661, 662; 568/383, 391, 449, 485, 487, 489

[56] References Cited

U.S. PATENT DOCUMENTS

| | | | |
|---|---|---|---|
| 3,894,110 | 7/1975 | Drehman | 585/660 |
| 4,132,668 | 1/1979 | Gryaznov et al. | 502/4 |
| 4,327,238 | 4/1982 | Eastman | 585/661 |
| 4,421,938 | 12/1983 | Windawi | 568/474 |
| 4,560,823 | 12/1985 | Gaffney | 585/654 |
| 4,675,465 | 6/1987 | Fanelli et al. | 585/654 |
| 4,737,595 | 4/1988 | Jones et al. | 585/654 |
| 4,769,509 | 9/1988 | Josefowicz | 585/400 |
| 4,927,763 | 5/1990 | Luetlens, Jr. et al. | 568/402 |

FOREIGN PATENT DOCUMENTS

| | | |
|---|---|---|
| 0460512 | 11/1991 | European Pat. Off. . |
| 0543535 | 5/1993 | European Pat. Off. . |

*Primary Examiner*—Ponnathapura Achutamurthy
*Attorney, Agent, or Firm*—Nixon & Vanderhye

[57] ABSTRACT

A process for the dehydrogenation of a hydrocarbon and/or oxygenated hydrocarbon feed, which process comprises the steps of (a) sequentially contacting the feed with a catalyst bed in a reaction chamber at elevated temperature, said catalyst bed comprising a first catalyst which is a dehydrogenation catalyst to produce a dehydrogenated product and hydrogen and a second catalyst capable of adsorbing and/or reacting with at least some of said hydrogen, said second catalyst having a porous coating.

(b) removing the dehydrogenated product and any hydrogen which has not been adsorbed or reacted from the reaction chamber;

(c) removing at least some of the adsorbed/reacted hydrogen from the coated catalyst and/or oxidising at least some of the reduced coated catalyst, thereby regenerating the second catalyst;

(d) using said regenerated second catalyst in step (a).

22 Claims, 2 Drawing Sheets

PROCESS FOR DEHYDROGENATION OF HYDROCARBON FEEDS

This application is a continuation of application Ser. No. 08/113,097 filed Aug. 30, 1993, now abandoned.

BACKGROUND OF THE INVENTION

The present invention relates to a process for the dehydrogenation of a hydrocarbon or oxygenated hydrocarbon feed.

Dehydrogenation processes, and in particular dehydrogenation of alkanes, are well known and employ a suitable dehydrogenation catalyst. In general, the feedstock is contacted with the catalyst to provide the dehydrogenated product and hydrogen. The hydrogen may then be separated from the product stream to provide the desired product.

EP-A-0543535 discloses a process for the dehydrogenation of a hydrocarbon feed which comprises contacting the feed with a dehydrogenation catalyst, optionally mixed with a catalyst for adsorbing or reacting with the hydrogen. Whilst the process of this European patent application provides good selectivities to the dehydrogenated product, it has been found that a proportion of the product is oxidised.

DESCRIPTION OF THE INVENTION

We have now found that the aforementioned problem may be overcome and selectivities to dehydrogenated products can be considerably improved by the presence of a special form of the second catalyst in the catalyst bed. Accordingly the present invention provides a process for the dehydrogenation of a hydrocarbon and/or oxygenated hydrocarbon feed, which process comprises the steps of (a) sequentially contacting the feed with a catalyst bed in a reaction chamber at elevated temperature, said catalyst bed comprising a first catalyst which is a dehydrogenation catalyst to produce a dehydrogenated product and hydrogen and a second catalyst capable of adsorbing and/or reacting with at least some of said hydrogen, said second catalyst having a porous coating.

(b) removing the dehydrogenated product and any hydrogen which has not been adsorbed or reacted from the reaction chamber;

(c) removing at least some of the adsorbed/reacted hydrogen from the coated catalyst and/or oxidising at least some of the reduced coated catalyst, hereby regenerating the second catalyst;

(d) using said regenerated catalyst in step (a)

The present invention provides a process for the dehydrogenation of hydrocarbons or oxygenated hydrocarbons wherein the dehydrogenation step and the hydrogen removal and subsequent steps are separated. The presence of a porous coating results in a preferential reaction of the hydrogen with the coated catalyst. Furthermore, the presence of a porous coating round the catalyst allows selective reaction of the catalyst with hydrogen, whilst preventing reaction with the dehydrogenated product. Consequently, further reactions of the dehydrogenated product is prevented, thus providing high yields. Additionally, the regeneration of the catalyst is unaffected by the coating.

The process of the present invention provides a method for dehydrogenating hydrocarbons or oxygenated hydrocarbons without the need for an external heat supply. High conversion rates can be obtained without the co-production of undesirable by-products. Preferably, step (c) is an oxidation of the coated catalyst, suitably using an oxygen-containing gas and the cyclic nature of the process avoids the simultaneous presence of free oxygen and hydrocarbon in the reactor minimising loss of selectivity through carbon oxide formation as experienced in other oxidative dehydrogenation processes.

The process of the present invention is suitably applicable to the dehydrogenation of alkanes to the corresponding alkenes. Suitably, the alkane has two to twenty carbon atoms. Suitably, the alkane feed may be a linear alkane with optionally one or more aryl groups or side chains. The preferred feed is a $C_2$ or $C_3$ or $C_4$ alkane. Alternatively, the hydrocarbon feed may comprise at least one oxygenated hydrocarbon such as an alcohol to provide aldehydes and/or ketones. Suitably, the feed may comprise an aliphatic alcohol having one to twenty carbon atoms. Preferably $C_1$ to $C_{10}$ alcohols are used, e.g. methanol, ethanol and propanol. The process of the present application is particularly preferred for the dehydrogenation of ethane to ethene.

The process may be operated at a conversion and selectivity sufficiently high so as to avoid distillative purification, hereby economising on plant and operating costs. Where the feed contains two or more different alkanes, the process may also be operated at a temperature sufficient to promote cracking for the co-production of mixtures of ethene, propene and butene from mixtures of ethane, propane, butane or higher hydrocarbons. In his even, if individual alkenes are required, distillative separation and purification of the mixed alkene product stream would be necessary.

The feed is contacted with a catalyst bed which comprises a dehydrogenation catalyst and a catalyst capable of selectively removing the hydrogen from the product stream. The dehydrogenation catalyst may be any suitable dehydrogenation catalyst well known to the person skilled in the art, e.g. such as platinum/zinc on silicalite; platinum/tin or palladium/tin on alumina; chromium oxide on alumina. Catalysts comprising a rare earth oxide and a metal selected from the group including nickel, palladium, platinum, copper, silver and gold may also be used as the dehydrogenation catalyst. Such catalysts may be capable of adsorbing hydrogen.

The catalyst bed comprises a second catalyst which is capable of adsorbing and/or reacting with the hydrogen formed in the dehydrogenation step to remove the hydrogen from the product stream. The second catalyst is provided with a porous coating. The porous coated catalyst should have a greater affinity for hydrogen than for oxygen than for water, otherwise water or oxygen could be preferentially retained. A suitable catalyst may, for example, be one that retains oxygen and converts hydrogen to water. Suitably, the catalyst may be any reducible oxide or hydrogen adsorber, optionally with a Group IB, IIB or group VIII metal and may be selected from the list including gold/ceria, nickel/ceria, iron/ceria, molybdenum oxide, tungsten oxide or any rare earth oxide.

The porous coating may be any suitable coating which is capable of allowing hydrogen to pass through the pores whilst inhibiting the passage of the dehydrogenated product. The porous coating may comprise one or more layers. The layers may suitably be of the same component or may be different. Suitably, the porous coating may be a membrane coating. The membrane coating may suitably be a zeo-type membrane. Suitable zeo-types for preparation of the membrane coating include KA (zeolite 3A), NaA (zeolite 4A), LiA, CaA, Erionite, K Erionite, Chabazite, Mordenite, MAPOs, SAPOs and ALPOs. The aforementioned zeolites are known in the arc and information of their structures is given in the "Atlas of Zeolite Structure Types" by Meier W M and Olsen D H, 1987, distributed by Polycrystal Book Service, Pittsburgh, USA. All of these zeo-types can be prepared by published literature methods. The zeo-type membrane may be prepared by any suitable method known to the person skilled in the art, for example as disclosed in European patent application No. 0460512, the disclosure of which is hereby incorporated by reference. The catalyst may be mixed with a gel precursor for the zeo-type membrane and the mixture heated at 50°–110° C. in order to deposit the membrane on the catalyst; this process may be repeated more than once.

Alternatively, the membrane coating may comprise an organometallic compound capable of reacting with the surface of the catalyst such that on decomposition there is provided an inert porous matrix. For the purposes of the present invention organometallic compounds include organosilicon and organoboron. The preferred compound is organosilicon which provides a silylated coating.

The silylated catalyst may be prepared by any suitable method. Suitably, the coated catalyst is contacted with a silylating agent under appropriate conditions. Suitable silylating agents include dimethyl dichlorosilane, trimethylchlorosilane, triethylchlorosilane, tri-n-propylchlorosilane and disilane such as hexamethyldisilane. The preferred silylating agent is dimethyl dichlorosilane. The silylating agent may be contacted with the coated catalyst either in the liquid or vapour phase.

The porous coated catalyst must be capable of adsorbing/ reacting with the hydrogen released in the dehydrogenation reaction. The hydrogen may be retained either chemically or physically or by a combination of both. By removing hydrogen, from the equilibrium during the dehydrogenation process, the reaction to the dehydrogenated product can be driven to completion.

The ability of the catalyst used with a porous coating to strongly adsorb/react with hydrogen under low partial pressures of hydrogen and at a temperature of 500° to 600° C. can be determined by measuring the adsorption/reaction isotherm after trapping any product water formed. The porous coated catalyst is suitably capable of adsorbing/ reacting with at least 2 ml of hydrogen per gram of coated catalyst at 500° C. at a hydrogen partial pressure of 0.00025 barA.

The hydrocarbon feed is contacted with a catalyst bed comprising the dehydrogenation catalyst and the porous coated catalyst. The two catalysts may be suitably mixed to provide an intimate mixture of separate pellets. The two catalysts may be admixed in weight ratios of suitably from 100:1 to 1:10 porous coated catalyst to dehydrogenation catalyst. The preferred admixture is from 20:1 to 1:1, especially preferred is a 10:1 admixture of porous coated catalyst to dehydrogenation catalyst.

The feed is firstly contacted with the catalyst bed to produce the dehydrogenated product and hydrogen. At least some, preferably all of the hydrogen produced is adsorbed by/reacted with the coated catalyst. Unadsorbed/unreacted hydrogen is removed from the reaction chamber. It is preferred that dehydrogenated product is free of hydrogen.

Where the hydrogen is adsorbed by the coated catalyst, the adsorbed hydrogen is removed from the coated catalyst. This step may suitably be carried out by contacting the catalyst with a component which is capable of being reduced by hydrogen. Suitably, the catalyst may be contacted with an oxygen-containing gas. The oxygen-containing gas may be suitably air or a synthetic gaseous mixture either richer or poorer in molecular oxygen than air. Oxygen itself may also be employed. Alternatively, the hydrogen may be removed by the action of heat, under vacuum, or through the action of a chemical reagent. Suitable chemical reagents include carbon dioxide and carbon monoxide. It is preferred that the catalyst bed is contacted with air. Where the hydrogen is reacted with the catalyst in step (a) of the process of the present invention, to form a reduced catalyst, the catalyst is then at least partly oxidised to regenerate it. Suitably, an oxygen-containing gas may be used for the oxidation step. Excess gas may be fed into the reaction chamber to limit the exhaust gas temperature such that unwanted side reactions are kept to a minimum.

The reaction of, for example, ethane and oxygen to ethene and water is exothermic giving an adiabatic temperature rise of about 1000° C. in air. This heat may be removed by performing the dehydrogenation reaction adiabatically, employing both the ethane feed and the molecular oxygen-containing gas feed at ambient temperature. If desired, the feed gases may be pro-heated, suitably by partial flow reversal. Pro-heating may reduce physical stress on the catalyst, but may also reduce the rate of heat removal from the catalyst into the passing gas, necessitating a larger bed and increasing the total gas flow required per unit of heat generated, i.e. per tonne of product produced.

The process of the present invention is of course cyclic. Cycle times which may be used will depend on factors such as bed dimension and gas velocity. Over the chosen cycle time, the heat capacity of a bed of solid material can be high compared to the gas passing through it such that a bed of the catalyst admixture should remain at approximately constant temperature over the cycle. The catalyst bed may be maintained at a uniform temperature by controlling the hydrogen adsorption capacity at each distance into the bed such that the cooling due to the gas flow over the cycle balances the heat produced at that position in the catalyst bed at burn off. This method of temperature control/stabilisation is made possible by the cyclic nature of the process and avoids the need for an expensive reactor with a large heat transfer area as used for conventional fixed bed exothermic reactions. A cycle may comprise the first step of feeding the alkane into the reactor which may take from one tenth to a quarter the time required to feed in the component to remove the hydrogen.

The elevated temperature at which the dehydrogenation process of step (a) is operated may suitably be in the range of from 150 to 200° C., preferably 300° to 700° C., especially 500° C. The pressure may suitably be atmospheric, but subatmospheric or elevated pressure may also be used.

BRIEF DESCRIPTION OF THE DRAWINGS

The process of the present invention will now be described in more detail with reference to the accompanying drawings in which.

DETAILED DESCRIPTION OF THE INVENTION

Figure 1:
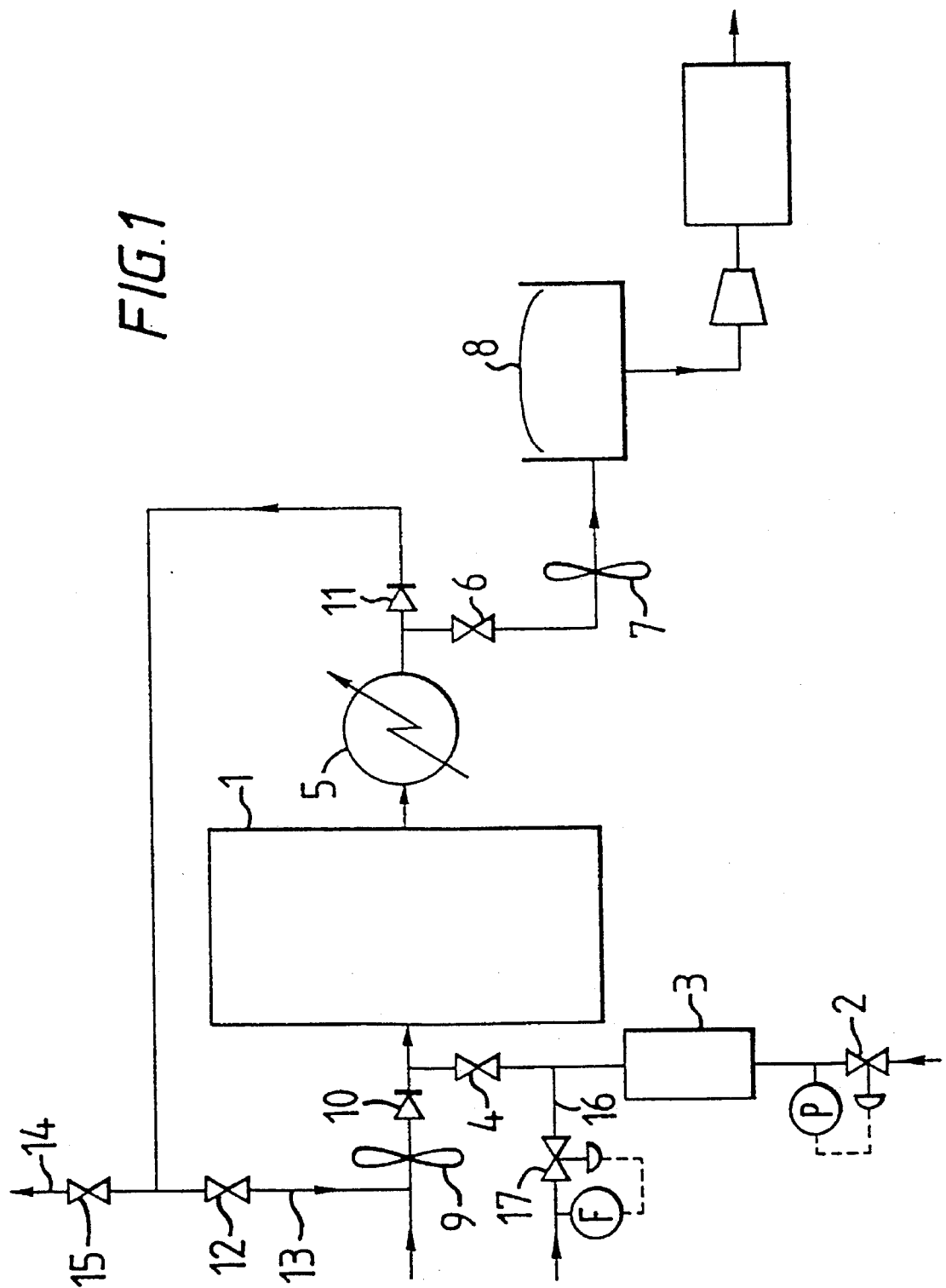
FIG. 1 is a process flow diagram of the process of the invention.

With reference to FIG. 1, cold ethane is fed for two seconds to a reactor (1) via a pressure control valve (2), a steam accumulator (3) and a timed valve (4). The reactor (1) contains a catalyst bed which comprises the catalyst admixture of the dehydrogenation catalyst and the porous coated catalyst, the porous coated catalyst being capable of adsorbing/reacting with hydrogen. The ethene produced is removed from the reactor through the heat exchanger (5) and the timed valve (6) by suction at slightly below atmospheric pressure by a blower (7) into a gasometer (8). Air is then driven by a blower (9) through a non-return valve.(10) into the reactor (1) for a period of 13 seconds, the timed valves (6) and (4) being closed. Combustion of the retained hydrogen, any carbon deposits on the catalyst and oxidation of the reduced oxide occurs thereby generating heat to maintain the catalyst temperature. Combustion gases exit from the reactor through the heat exchanger (5) and non-return device (11). A sufficient portion of the combustion gas is recycled to reactor 1 via damper (12) and line (13) to the air feed in order to ensure that the oxygen concentration is below the flammable limit for safety reasons, and that the inlet temperature of the gas into reactor 1 is warmed above the dew point; the remainder of the combustion gas leaves through line 14 via damper (15).

At the end of the 15 seconds cycle, timed valve (4) opens allowing a "pig" of steam to be admitted to the reactor through line 16 from accumulator (3) where steam has been accumulating because of its continuous admission through valve (17). The "pig" of steam serves to flush any remaining flue gases from the reactor and separate the ethane and air. Alternatively, inert gases such as nitrogen or helium may be used.

The timed valves (4 and 6) are controlled by a timer (not shown). Adjustment of the timer is used to control the ethane feed per cycle to match the hydrogen adsorption capacity of the catalyst. Flow during the ethane phase is controlled to match or be less than the bed activity. Too little feed per cycle could manifest itself in a distorted temperature profile through the catalyst bed, particular high at the inlet. Too little catalyst activity could show as a distorted temperature profile and a high residual ethane content in the gases leaving reactor 1.

Bed temperature can be controlled by adjusting the admission time period and velocity of the air feed. A longer admission time for air gives lower catalyst temperatures, particularly at the inlet. Higher air flow rates reduce the catalyst temperature, particularly at the outlet.

The foregoing description assumes an ethane pressure greater than blower discharge and an ethylene pressure below atmospheric pressure, so that the non return devices can functions. Flow through the reactor during the ethane input would be slightly greater than during the air input phase because of the extra pressure drop.

EXAMPLES

Example 1

Preparation of Dehydrogenation Catalyst (0.5 wt % Pt/4.0 wt % Zn/Silicalite)

The dehydrogenation catalyst was prepared according to European Patent Application No. 89306106.9 wherein 600 g of an aqueous solution containing 20% by weight tetrapropylammonium hydroxide (TPAOH) was added with stirring to 200 g of an ammonia stabilised aqueous silica slurry sold under the Trade Mark Ludox AS40 by Dupont containing 40% by weight silica. The resultant hydrogel had the molar composition of 4.4 TPAOH:1.4 $NH_3$:100$SiO_2$:700 $H_2O$ The hydrogel was heated at 175° C. for 72 hours in a pressure vessel under autogenous pressure. The vessel was then cooled and the product filtered, washed and dried at 100° C. The X-Ray powder diffraction pattern showed that the product was silicalite-1.

The silicalite sample was calcined at 600° C. in air for 48 hours. It was then stirred in 20% by weight nitric acid (silicalite/solution—0.25% by weight) for 1 hour at room temperature, filtered, washed with distilled water, dried and calcined again at 600° C. for 16 hours.

The treated silicalite (30 g) was mixed with 150 g of an aqueous solution containing 4.2 g of Zn $(C_2H_3O_2)_2.2H_2O$ and the mixture dried in a rotary evaporator under vacuum. The solid was then calcined at 500° C. in air for 16 hours. The Zn impregnated solid was mixed with 150 g of aqueous solution containing 0.24 g of Pt $(NH_3)_4Cl_2.H_2O$. The mixture was dried in a rotary evaporator under vacuum.

The catalyst was then reduced in flowing hydrogen (100 $cm^3$/min/$cm^3$ catalyst) at 530° C. for 24 hours before purging in an inert gas and cooling to room temperature.

Example 2

Preparation of Zeolite 4A Coated Gold/Ceria Catalyst

2a) A solution of cerous nitrate hexahydrate (10 g) and hydrogen tetrachloroaurate (2 g) in 25 $cm^3$ of water was added dropwise with stirring to a saturated aqueous solution (800 $cm^3$) of ammonium bicarbonate. The resultant precipitate was separated by filtration and washed three times by redispersing in 500 $cm^3$ of water followed by filtering. The washed precipitate was then dried at 110° C. for 18 hours before crushing and sieving to give particles of 1 mm diameter. The catalyst particles were then heated under flowing air or an inert gas at a flow rate of 100 $cm^3$ per minute from room temperature to 500° C. at a heating rate of 2° C. per minute; held at 500° C. for 10 hours and then cooled to room temperature. The resulting catalyst was found to have 15% w/w gold and a surface area of 80 $m^2$ per gram. The catalyst was then analysed for hydrogen adsorption/reaction capability and showed a capability of 5 $cm^3$/g at 500° C. under a hydrogen partial pressure of 0.00025 barA.

2b) A zeolite gel was prepared by adding 5.66 g of sodium aluminate (38% $Na_2O$/61% $Al_2O_3$ by weight) to 13.4 g sodium silicate solution (ex BDH) and 0.574 g sodium hydroxide. 80 $cm^3$ of water was then added and the resulting mixture stirred vigorously for 5 minutes to obtain the gel.

A weight of 6 g of the gold/ceria catalyst and 40 $cm^3$ of the zeolite gel were placed in a PTFE lined autoclave bomb (50 $cm^3$ volume). The bomb was sealed and heated to 90° C. and kept at this temperature for 16 hours. The bomb was then cooled to room temperature, opened and the contents filtered, washed several times with distilled water and dried in air at 110° C. for 1 hour. The dried catalyst was sieved to remove the fine excess zeolite from the coated gold ceria catalyst. The above zeolite coating stage was repeated a further four times using fresh zeolite gel each time. The resulting catalyst was coated with the membrane coating.

Example 3

Preparation of Silylated Zeolite 4A Coated Gold/Ceria Catalyst

A weight of 1 g of the coated gold/ceria catalyst prepared as described in Example 2 was placed in a quartz tube (¼ inch outer diameter) inside a furnace. Dry nitrogen was passed over the catalyst at a rate of 50 ml/min. The temperature of the furnace was increased to 500° C. at a rate of 10° C./min. The temperature was maintained at 500° C. for 1 hour prior to diverting the nitrogen flow to become saturated with water vapour at 25° C. The saturated gaseous stream was then allowed to flow over the catalyst for 1 hour. The pure nitrogen flow was then restored to the catalyst. The nitrogen flow was then diverted to become saturated with dimethyldichloro silane vapour at 25° C. The saturated gaseous stream was then allowed to flow over the catalyst for 1 hour. The pure nitrogen purge was then restored to the catalyst and after a further hour the temperature was reduced to ambient.

The catalyst was removed from the furnace, placed in a muffle furnace and heated in air at a rate of 1° C./min to 500° C. After 8 hours at 500° C., the temperature was reduced to ambient and the catalyst removed from the furnace.

Example 4

Preparation of Silylated Gold/Ceria Catalyst

A weight of 1 g of gold/ceria catalyst prepared as described in Example 2a was silylated according to the process of Example 3.

Example 5

Dehydrogenation of Ethane

The process was carried out as described above with reference to FIG. 1 using a gaseous stream of ethane (25% v/v in helium) at a temperature of 500° C., a pressure of 1 barA and a flow rate of 40 cm$^3$/min (at STP). The gaseous stream was passed over the catalyst bed containing an intimate mixture of the zeo-type coated catalyst (2.35 g) as disclosed in Example 2 and the dehydrogenation catalyst (0.3 g) as prepared in Example 1. The subsequent regeneration was carried out at the same temperature, pressure and flow rate using 20% v/v oxygen in helium. An intermediate purge with helium was used rather than steam to separate the ethane and oxygen containing gases.

(i) Ethane Addition

Gas chromatographic and mass spectral analysis of the exit gas stream confirmed that a high conversion of ethane to ethene was obtained with little hydrogen being present. Water and small amounts of methane and carbon dioxide were also found in the exit gas stream. The concentration of ethene reached a maximum of 7.5% v/v before decreasing to the thermodynamic equilibrium value of 2% v/v as the hydrogen concentration increased in the exit gas due to the hydrogen adsorption/reaction capacity of the ceria becoming saturated.

(ii) Regeneration

Water was released along with a small quantity of carbon dioxide during the regeneration step of the cycle as oxygen breakthrough occurred.

The cumulative performance data calculated through a complete process cycle (starting at the regeneration stage) gave a cumulative ethane conversion of approximately 33% with a cumulative ethene selectivity of 82% at the maxima in ethene productivity.

Example 6

Dehydrogenation and Regeneration of Ethane under Continuous Operation

The process of Example 5 was carried out under continuous operation using the catalyst mixture, temperature, pressure, gas concentrations and flow rates as described in Example 5. The ethane and oxygen containing gases were separated by a helium purge (40 cm$^3$/min). The period of one cycle in this example was 2 minutes. This cycle was made up of 30 seconds ethane addition, 30 seconds purge, 30 seconds oxygen addition and 30 seconds purge. For the catalyst volumes and flow rates used, the time of ethane addition was approximately that calculated to give a maximum in the productivity of ethene.

Over a 14 minute period of time gas chromatographic and mass spectral analysis showed that the cumulative conversion of ethane was 37% and the cumulative selectivity to ethene was 60% (based on total carbon). The selectivity is slightly lower than that obtained in Example 5 since the process was carried out with a severely aged catalyst mixture.

Example 7

A sample of zeolite coated/ceria catalyst (0.2 g) prepared according to the method of Example 2 was loaded into the sample tube of differential scanning calorimeter (DSC) apparatus. A similar weight of quartz glass pieces was loaded into the reference tube. Helium was flowed through the tubes (ca. 16 ml/min). The samples were heated at 10° C./min to 500° C. and held at this temperature.

The gas flow was changed to 5% argon in ethylene (ca. 16 ml/min) for 500 seconds, then the sample and reference purged for 300 seconds with helium. The gas flow was changed to 20% oxygen in helium (ca. 16 ml/min) for 500 seconds, then the sample and reference purged for 300 seconds with helium.

The gas flow was changed to hydrogen (ca. 16 ml/min) for 500 seconds, then the sample and reference purged for 300 seconds with helium. The gas flow was changed to 20% oxygen in helium (ca. 16 ml/min) for 500 seconds, then the sample and reference purged for 300 seconds with helium.

Figure 2:
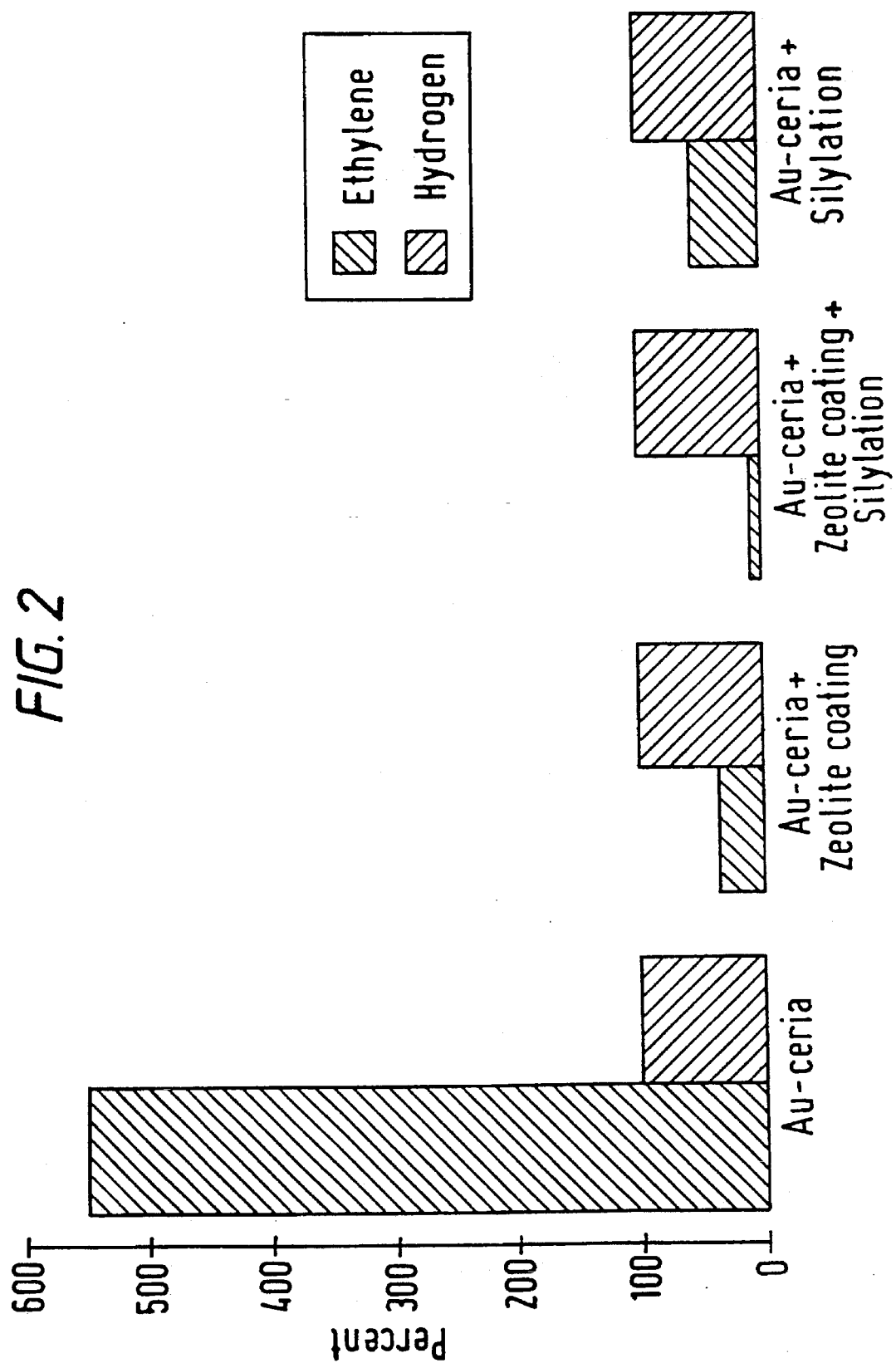
FIG. 2 shows the percentage amounts of hydrogen and ethylene produced according to the experiments described in Example 7–9 and Comparative Example 1.

Results are given in FIG. 2.

Example 8

The process of Example 7 was repeated using a silylated zeolite coated gold/ceria prepared according to the method of Example 3. Results are given in FIG. 2.

Example 9

The process of Example 7 was repeated using a silylated gold/ceria prepared according to the method of Example 4. Results are given in FIG. 2.

Comparative Example 1

The process of Example 7 was repeated using a sample of gold/ceria catalyst prepared according to the method of Example 2a Results are given in FIG. 2.

With reference to FIG. 2, the results are derived for the determination of hydrogen and ethylene reactivity as follows: Hydrogen—The heat released during the oxidation of the catalyst after 500 seconds exposure to hydrogen and 300 seconds purging in helium, all at 500° C. This is determined 100% heat release. Ethylene—The heat released during the oxidation of the catalyst after 500 seconds exposure to 5% argon in ethylene and 300 seconds purging in helium, all at 500° C. For each example this heat release has been reported relative to that for hydrogen i.e.

$$\frac{\text{ethylene heat release}}{\text{hydrogen heat release}} \times 100$$

It can be seen from FIG. 2 that the zeolite coated gold/ceria and the silylated zeolite coated gold/ceria catalysts are least reactive to ethylene.

We claim:

1. A process for the dehydrogenation of a hydrocarbon or oxygenated hydrocarbon feed, said process comprising the steps of:

(a) contacting the feed with a catalyst bed in a reaction chamber at elevated temperature, said catalyst bed comprising a dehydrogenation catalyst and a hydrogen retention agent, said hydrogen retention agent being in particulate form and having a porous coating, said dehydrogenation catalyst producing a product stream comprising a dehydrogenated product and hydrogen, said porous coated hydrogen retention agent being capable of selectively removing and adsorbing hydrogen from said product stream;

(b) removing from the reaction chamber the dehydrogenated product and any hydrogen which has not been adsorbed by said porous coated hydrogen retention agent;

(c) removing at least some of the adsorbed hydrogen from said porous coated hydrogen retention agent, thereby regenerating said porous coated hydrogen retention agent; and (d) using the regenerated porous coated hydrogen retention agent, in step (a).

2. A process according to claim 1, wherein said porous coated hydrogen retention agent is capable of reacting with at least some of the hydrogen to form a reduced coated hydrogen retention agent.

3. A process according to claim 2, wherein in step (c), at least some of the reduced coated hydrogen retention agent is oxidized to regenerate the porous coated hydrogen retention agent.

4. A process according to claim 1 in which the hydrocarbon feed comprises one or more alkanes.

5. A process according to claim 4 in which the alkane is $C_2$, $C_3$ or $C_4$ alkane.

6. A process according to claim 1 in which the oxygenated hydrocarbon is an alcohol.

7. A process according to claim 6 in which the alcohol is a $C_1$ to $C_{20}$ alcohol.

8. A process according to claim 1, in which the porous coating is a membrane coating.

9. A process according to claim 8, in which the membrane is a zeo-type membrane.

10. A process according to claim 9, in which the zeo-type membrane is selected from the group consisting of KA (zeolite 3A), NaA (zeolite 4A), LiA, Erionite, K Erionite, Chabazite, Mordenite, MAPOs, SAPOs and ALPOs.

11. A process according to claim 8, in which the membrane coating is obtained from the decomposition of an organometallic compound capable of reacting with the surface of the hydrogen retention agent.

12. A process according to claim 11, in which the organometallic compound is organosilicon.

13. A process according to claim 8, wherein the membrane coated hydrogen retention agent and the dehydrogenation catalyst are present in a weight ratio of 100:1 to 1:10.

14. A process according to claim 1, in which the hydrogen is removed from the dehydrogenation catalyst in step (c) by contacting the catalyst with an oxygen-containing gas, thereby providing heat to maintain the catalyst bed at the elevated temperature.

15. A process according to claim 14, in which the elevated temperature is 300 to 700° C.

16. A process for the dehydrogenation of a hydrocarbon or oxygenated hydrocarbon feed, said process comprising the steps of:

(a) contacting the feed with a catalyst bed in a reaction chamber at elevated temperature, said catalyst bed comprising a dehydrogenation catalyst and a hydrogen retention agent, said hydrogen retention agent being in particulate form and having a porous coating, said dehydrogenation catalyst producing a product stream comprising a dehydrogenated product and hydrogen, said porous coated hydrogen retention agent being capable of adsorbing at least some of the hydrogen and reacting with least some of the hydrogen to form a reduced coated hydrogen retention agent;

(b) removing from the reaction chamber the dehydrogenated product and any hydrogen which has not been adsorbed by and reacted with said porous coated hydrogen retention agent;

(c) removing at least some of the adsorbed hydrogen from said porous coated hydrogen retention agent, and oxidizing at least some of the reduced coated hydrogen retention agent, thereby regenerating the porous coated hydrogen retention agent; and (d) using the regenerated porous coated hydrogen retention agent in step (a).

17. A process for the dehydrogenation of a hydrocarbon or oxygenated hydrocarbon feed, said process comprising the steps of:

(a) contacting the feed with a catalyst bed in a reaction chamber at elevated temperature, said catalyst bed comprising a dehydrogenation catalyst and a hydrogen retention agent, said hydrogen retention agent being in particulate form and having a porous coating said dehydrogenation catalyst producing a product stream comprising a dehydrogenated product and hydrogen, said porous coated hydrogen retention agent being capable of reacting with least some of the hydrogen to produce a reduced coated hydrogen retention agent;

(b) removing from the reaction chamber the dehydrogenated product and any hydrogen which has not been adsorbed by and reacted with said porous coated hydrogen retention agent;

(c) oxidizing at least, some of said reduced coated hydrogen retention agent, thereby regenerating the porous coated hydrogen retention agent; and (d) using said regenerated porous coated hydrogen retention agent in step (a).

18. A process according to claim 1, wherein said porous coated hydrogen retention agent is capable of retaining at least two ml of hydrogen per gram of coated hydrogen retention agent at 500° C.

19. A process according to claim 1, wherein said dehydrogenation catalyst comprises a rare earth metal oxide and a metal selected from the group consisting of nickel, palladium, platinum, copper, silver and gold.

20. A process according to claim 1, wherein said dehydrogenation catalyst is selected from the group consisting of platinum/zinc on silicalite, platinum/tin on alumina, palladium/tin on alumina, and chromium oxide on alumina.

21. A process according to claim 1, wherein said porous coated hydrogen retention agent comprises a reducible metal oxide and a metal selected from the groups consisting of a Group IV, IIB and VIII metal of the Periodic Table.

22. A process according to claim 21, wherein said metal is selected from the group consisting of gold, nickel and iron, and said reducible metal oxide is selected from the group consisting of ceria, molybdenum oxide and tungsten oxide.

* * * * *